United States Patent [19]

Somazzi et al.

[11] Patent Number: 5,670,610
[45] Date of Patent: Sep. 23, 1997

[54] NEW CATALYTIC SYSTEM AND PROCESS FOR THE COPOLYMERIZATION OF OLEFINS WITH CARBON MONOXIDE

[75] Inventors: Anna Somazzi, S. Margherita; Gabriele Lugli, S. Donato; Fabio Garbassi, Novara, all of Italy

[73] Assignee: Enichem S.p.A., Milan, Italy

[21] Appl. No.: 457,816

[22] Filed: Jun. 1, 1995

Related U.S. Application Data

[62] Division of Ser. No. 348,126, Nov. 28, 1994, Pat. No. 5,556,823.

[30] Foreign Application Priority Data

Dec. 3, 1993 [IT] Italy .................. 002538 A/93

[51] Int. Cl.$^6$ .................. C08G 67/02; B01J 31/18
[52] U.S. Cl. .................. 528/392; 528/392; 502/162; 502/165; 502/167; 502/169
[58] Field of Search .................. 528/392; 502/162, 502/165, 167, 169

[56] References Cited

U.S. PATENT DOCUMENTS

| | | | |
|---|---|---|---|
| 4,446,329 | 5/1984 | Waller | 585/458 |
| 4,874,736 | 10/1989 | Drent | 502/165 |
| 5,245,123 | 9/1993 | Drent et al. | 528/392 |
| 5,346,873 | 9/1994 | Somazzi et al. | 502/165 |
| 5,369,073 | 11/1994 | Somazzi et al. | 502/162 |

*Primary Examiner*—Samuel A. Acquah
*Attorney, Agent, or Firm*—Oblon, Spivak, McClelland, Maier & Neustadt, P.C.

[57] ABSTRACT

An active catalyst in the preparation of alternating copolymers of olefins with carbon monoxide (CO) and consisting of:

a) a metal salt of the group IB of the periodic table;
b) a bidentate binder containing two nitrogen or phosphorous atoms capable of binding themselves to the metal atom by means of co-ordination bonds;
c) a Lewis acid;
d) optionally an oxidizing agent.

The preparation of the catalyst is described together with its use in the alternating copolymerization of ethylene (C2) and/or other olefins with carbon monoxide.

20 Claims, No Drawings

NEW CATALYTIC SYSTEM AND PROCESS FOR THE COPOLYMERIZATION OF OLEFINS WITH CARBON MONOXIDE

This is a division of application Ser. No. 08/348,126 filed on Nov. 28, 1994 now U.S. Pat. No. 5,556,823.

The present invention relates to a catalyst based on copper, silver or gold, its preparation and use in the copolymerization of ethylene (C2) and/or other olefins with carbon monoxide (CO) to produce perfectly alternating copolymers.

Catalytic systems capable of producing alternating C2—CO polymers are known and widely described in the art. They are mainly catalytic systems based on metals belonging to the eighth group of the periodic table.

For example, U.S. Pat. No. 3,984,388 discloses the use of Ni cyanide as polymerization catalyst of C2/CO mixtures. Other sources of non-patent literature [Makromol. chem., 161,11741 (1968)], describe the possible use of cobalt-carbonyls.

Numerous patents describe the use of catalytic systems based on salts of Pd, or other metals belonging to the eighth group of the periodic table, and containing bidentate binders capable of binding themselves to the metal atom by means of co-ordination bonds; these catalytic systems are capable of copolymerizing with alternating copolymers ethylene (C2) and/or other compounds containing unsaturations of the olefinic type with carbon monoxide (CO) both in solution and in suspension, in the presence of a mineral and/or organic acid.

For example, G.B. patent 1.081.304 discloses the polymerization in solution of monomeric mixtures of C2 and CO to give alternating copolymers with the use of an alkylphosphinic complex of a Pd salt whereas U.S. Pat. No. 3,689,460 claims a catalyst based on a tetrakisphosphinic complex of palladium. Similar catalytic systems are described in U.S. Pat. No. 3,694,412.

Other catalytic systems known in the art, capable of producing alternating C2—CO copolymers, consist of: 1) a salt of palladium, nichel or cobalt of an acid preferably carboxylic, 2) a bidentate base, generally consisting of an alkyl or cycloalkyl hydrocarbon symmetrically substituted by two dialkyl or diphenylphosphinic groups or two groups containing at least one nitrogen atom, 3) an anion of an acid, preferably an organic acid, with pKa of about 2. These catatytic systems are described for example in patents EP 0121965, EP 0222454, EP 0257663, EP 0305012 and enable alternating C2—CO polymers to be obtained with good yields.

Variations in what is specified above consist in the addition of a fourth component to the catalytic system, selected from compounds belonging to the group of quinones, organic oxidants or aromatic nitrocompounds, according to what is claimed for example in European patents EP 239145 and EP 245893, or in the use of bidentate bases with the two heteroatoms consisting of nitrogen or mixed P and S heteroatoms, as described for example in European patents EP 245893 and EP 343734.

Catalytic systems are also known in the art based on Palladium salts, capable of copolymerizing with alternating copolymers ethylene (C2) and/other compounds containing unsaturations of the olefinic type with carbon monoxide (CO) in a gas phase in the presence of a Lewis acid or a mixture of Lewis acid-Bronsted acid.

For example, in patent EP 0501572 a mixture (1:1) is used of Lewis acid/Bronsted acid. The Lewis acid is preferably a fluoride and in particular a fluoride selected from borontrifluoride, titanium tetrafluoride, phosphorous pentafluoride; the Bronsted acid is preferably hydrogen fluoride. The catalytic system, dissolved in a small quantity of methanol, is absorbed on a support (for example silica, allumina and preferably previously prepared ethylene-CO copolymer).

The presence of the Bronsted acid can be eliminated; for example in patent EP 0508502 Lewis acids are used.

European patent application 93200697 and Italian patent application MI-92-A-002820 respectively describe alternating copolymers of carbon monoxide with an olefin such as ethylene, propylene, etc.; the copolymerization takes place in the presence of a homogeneous catalyst based on: 1) a salt of a metal of the group IB of the periodic table; 2) a bidentate binder containing two phosphorous or nitrogen atoms; 3) an organic or inorganic acid.

The Applicant has now unexpectedly found that it is possible to prepare alternating copolymers of carbon monoxide with an olefin or mixture of olefins, such as ethylene (C2), propylene, butene, and/or higher homologous products, in the presence of a catalyst based on:

1) a salt of a metal of the group IB of the periodic table,
2) a bidentate binder, consisting of a compound (binding base) containing two phosphorous or nitrogen atoms capable of binding themselves to the Cu, Ag or Au atom by means of co-ordination bonds,
3) a Lewis acid.

To improve the polymer yields, a fourth component consisting of an organic or inorganic oxidizing agent can be added to the above catalytic system.

In accordance with this, a first aspect of the present invention relates to a catalytic system, active in the preparation of alternating copolymers of olefins with carbon monoxide (CO), consisting of:

a) a Cu, Ag or Au salt
b) a bidentate chelating base, containing two phosphorous or nitrogen atoms,
c) a Lewis acid
d) optionally an organic or inorganic oxidizing agent.

The catalysts defined above can be used in a homogeneous phase or heterogeneous phase, after being absorbed on suitable organic or inorganic supports such as silica, allumina or the same C2/CO copolymer previously prepared.

The present invention also relates, and this represents a second aspect of the present invention, to the use of this catalytic system in the alternating copolymerization of ethylene (C2) and/or other olefins with carbon monoxide (CO).

The copper, silver or gold salts which can be used as component a) of the catalytic system of the present invention are generally inorganic, organic or organometallic salts which are soluble in common organic solvents such as for example methanol, toluene, dimethoxyethane; the solvents will be more clearly described hereafter. Examples of Cu, Ag or Au salts, which do not limit the purposes of the present invention, are trifluoromethanesulphonate, trifluoroacetate, acetate, toxilate, sulphate, chloride, hexafluorophosphate and diethylcarbamate.

The bidentate chelating bases which can be used as component b) of the catalytic system of the present invention are compounds containing two heteroatoms such as two phosphorous or nitrogen atoms capable of binding themselves to the Cu, Ag or Au atom by means of co-ordination bonds and corresponding to the general formula (I)

$$R_1R_2\text{-M-R-M-}R_3R_4,$$

wherein:

M represents a phosphorous or nitrogen atom;

R represents a polymethylene radical containing from 2 to 4 carbon atoms, a cycloalkylidene radical containing from 2 to 10 carbon atoms, an ortho-phenylene radical;

$R_1$ and $R_2$, $R_3$ and $R_4$, the same or different, represent an alkyl radical containing from 1 to 6 carbon atoms, a cycloalkyl radical containing from 3 to 6 carbon atoms, an aromatic radical containing from 6 to 12 carbon atoms, possibly with substituents.

As the bidentate chelating base is capable of forming a complex with the metal atom (Cu, Ag or Au) through its two heteroatoms, the total number of atoms forming the ring of the complex is preferably not higher than 7, which means that the total number of carbon atoms of the polymethylene radical R, is preferably not higher than 4; if instead R consists of a cycloalkylidene radical, the latter preferably has the two chelating atoms bound to two adjacent atoms in the ring.

On the basis of what is specified above, examples of bidentate chelating bases containing two phosphorous atoms are: 1,3-bis(diphenylphosphine)propane, 1,4-bis(dicyclohexylphosphine)butane, and 1,2-bis(diphenylphosphine)cyclohexane; other bidentate bases containing two nitrogen atoms, which do not belong to the group of chelating compounds represented by general formula (I) but which can be used in the formation of the catalytic systems of the present invention are 1,10-phenanthroline, 3-methyl-1,10-phenanthroline, 2,2'-bipyridyl and 4,4'-dimethyl-2,2'-bipyridyl.

Component c) of the catalytic system of the present invention is a Lewis acid with general formula $AX_n$, wherein n=3 or 5 or its addition products with bases, wherein A can be B, Al, Ga, In, As, P, Sb;

X is a halogen, an aliphatic, aromatic monovalent radical or its corresponding substitutes.

Lewis acids which can be used for the purposes of the present invention are: borotrifluoride (BF3), borotrifluoride etherate (BF3.Et$_2$O), antimonium pentafluoride (SbF5), Arsenic pentafluoride (AsF5), gallium trifluoride (GaF3), alluminium trichloride (AlCl3), borotrichloride (BCl3), borotribromide (BBr3), alluminium tribromide (AlBr3), tris-(pentafluorophenyl)-boro [B(C6F5)$_3$] wherein R=H, alkyl, cycloalkyl, NaBF4, NH4PF6, NaB(C6H5)$_4$.

Lewis acids preferably used for the purposes of the present invention are borotrifluoride, alluminium trifluoride and tris-(pentafluorophenyl)-boron.

To increase the activity of the catalyst, an oxidizing agent can be incorporated into the catalytic system as component d); for this purpose 1,4-quinonic compounds can be used for example such as 1,4-benzoquinone or 1,4-naphthoquinone, or nitroaromatic compounds such as nitrobenzene or nitronium fluoroborate (NOBF4).

The final catalytic system is obtained by adding to a solution of component a) in a suitable solvent, the other two components of the catalytic system, component b), i.e. the bidentate base and component c), or the Lewis acid respectively; the addition is carried out at room temperature in an inert atmosphere (nitrogen).

If component d), an oxidizing agent, is used, it is added to the catalytic system as previously prepared.

The solution thus obtained is then ready to used in the synthesis of alternating polymers.

If a copper salt is used as component a) of the catalyst, this is obtained by adding a bidentate binder containing two phosphorous atoms, for example 1,3 bis(diphenylphosphine) propane (DPPP), to a solution of copper acetate Cu(CH$_3$COO)$_2$ in methanol, and then a Lewis acid such as borotrifluoride or tris-(pentafluorophenyl)-boron. Valid examples of preferred fourth component d) of the catalytic system are 1,4-benzoquinone, 1,4-naphthoquinone or nitronium fluorobotate (NOBF4).

The molecular ratio between the metal salt and bidentate binder to be added to the reaction medium can vary within a wide range; in the preferential case that component b) consists of a bis(diphenylphosphine)alkane such as for example 1,3-bis(diphenylphosphine)propane, this ratio is generally between the values 1/1 and 1/4 moles of salt/moles of bidentate base; a ratio of 1/1 is however preferred.

The molar quantity of component c) depends in turn on its nature and the quantity of component a). In the preferential case in which component c) consists of BF3 or B(C6F5)$_2$, the latter is added to the reaction medium in a quantity of between 0.5 and 200 moles of acid/mole of metal salt; the molar quantity of component c) is preferably between 1 and 50 moles per g. of metal atom.

The molar ratio of component d) with respect to a) can be between 10 and 150 and, preferably, between 50 and 100.

Solvents of the formation reaction of the catalytic complex of the present invention which can be used are: aliphatic, aromatic hydrocarbons, mixed mixtures aromatics-aliphatics, hydroxylated solvents such as alcohols and glycols, linear or cyclic ethers such as for example diethylether, dimethoxiethane and tetrahydrofuran; the selection of the most suitable solvent is made each time according to the solubility of the metal salt and bidentate compound without jeopardizing the activity of the final catalytic system.

An objective advantage of the present invention lies in the fact that the catalytic system is characterized by considerable flexibility and requires materials which are available on the market and/or can be easily prepared, with great simplification of the productive process; in particular copper salts, as component a) of the catalytic system, as well as the bidentate base b) and component c) and optional component d) are relatively inexpensive products.

The preparation of the catalytic system is carried out in a homogeneous phase by adding the bidentate base, the desired quantity of component c) and finally component d) when present to the metal salt of group IB, dissolved in methanol or in a mixture methanol/tetrahydrofuran (THF) or aromatic solvents. The resulting solution can be used as such or can be absorbed on an inert solid support (silica, allumina) or on the alternating C2—CO polymer itself, previously prepared. In this case a hetergenized catalyst is obtained which can be used for carrying out the polymerization in a heterogeneous phase (slurry) or gaseous phase.

A second aspect of the present invention relates to the use of the catalytic system described above in the copolymerization of CO with one or more monomers containing olefinic unsaturations to obtain alternating CO/olefin copolymers with good yields, as will be shown in the enclosed examples.

The rigorous alternation of the copolymer obtained according to the present invention was verified using a spectroscopic method as indicated in literature and precisely in "Application of Polymer Spectroscopy", published by Academic Press (1978), page 19.

The copolymerization reaction can be carried out, as already specified, using a process in both a liquid and gas phase. In the case of a process in a liquid phase, the polymerization is carried out by introducing in order the homogeneous or heterogeneous catalyst as previously prepared and the reaction solvent into the polymerization reactor and pressurizing with the mixture of monomers to the required pressure. The mixture is heated to the desired temperature and the polymerization is carried out isothermally and for the desired time. The polymerization temperatures are between 50° and 120° C. The pressurization is carried out up to a pressure of between $40 \times 10^5$ and $100 \times 10^5$ Pa and for a polymerization time of between 3 and 9 hours.

The polymerization solvent can be alcohol, ether, hydrocarbon or a mixture of two or more of the above solvents, provided that, when the solvent consists of an ether or hydrocarbon or their mixtures, a suitable quantity of alcoholic solvent must in any case be present, conveniently added or resulting from the preparation of the catalytic system. The quantity of catalyst, expressed in grams-atom of metal per liter of solvent, is between the values $10^{-2}$ and $10^{-5}$ and the other components of the catalytic system, component b), c) and d) respectively are used in the above molar ratios.

The polymerization reaction is preferentially carried out in an alcoholic solvent, containing the catalytic system, with mixtures 1/1 molar ratio CO/olefins, at pressures of $50 \times 10^5$–$60 \times 10^5$ Pa, temperatures of between 70° and 90° C., and for a polymerization time of between 3 and 6 hours.

The polymerization in a gas phase is characterized in that the monomers are put in contact with the catalyst without a solvent. For the preparation of polymers on an industrial scale, polymerization in a gas phase is preferred to polymerization in a liquid phase as in a gas phase the filtration and centrifugation operations for recovering the copolymer formed as well as the distillation of the polymerization solvent can be omitted as they are too expensive. For polymerization in a gas phase the catalyst can be prepared in different ways. The polymerization in a gas phase is preferably carried out using the catatyst deposited on a solid support. The deposit of the catalyst can be obtained by putting the support in contact with a solution of the catalyst in a suitable solvent and then totally or partially removing the solvent under vacuum at room temperature. The catalyst thus prepared is introduced into the polymerization environment together with small quantities of methanol as explained in the experimental part. Preferred solvents are alcohols and in particular methanol. The support materials to be used for the deposit of the catalyst can be of an organic or inorganic nature. Examples of supports which can be used are: silica, allumina, talc, cellulose, etc. Polymers such as polyethylene, polypropylene, polystyrene and olefin/CO copolymers previously prepared, can also be used as support.

The olefinic monomers which can be used alone or mixed with two or more together with the carbon monoxide are alpha-olefins such as ethylene, propylene, butene-1, pentene-1, etc., cyclopentene and styrene. The preferred monomer is ethylene (C2), whereas the preferred mixture is ethylene with propylene.

The possibility of being able to use different olefins, either alone or together, for the production of the copolymers of olefins with carbon monoxide, is another advantage of the present invention. In this way it is possible to obtain an alternating copolymer whose properties, for example melting point, glass transition temperature (Tg) and processability, can be modulated.

Following this description of the general aspects of the present invention, the examples below have the sole purpose of illustrating some of the details, but should in no way be considered as limiting the present invention.

EXAMPLE 1

500 cm$^3$ of methanol containing 0.5 mmoles of Cu(CH$_3$COO)$_2$, 0.5 mmoles of 1,3-bis(diphenylphosphine) propane (DPPP), 10 mmoles of BF3 etherate and 40 mmoles of p-benzoquinone, are charged into a 1 liter autoclave previously fluxed with nitrogen. A 1/1 molar mixture of ethylene/CO is then added until a pressure of $56 \times 10^5$ Pa is reached.

After 5 hours of reaction at 80° C., the autoclave is cooled to room temperature and the residual pressure is discharged. The copolymer is filtered, washed with methanol and dried at a temperature of about 60° C. and with a vacuum of $10^2$ Pa. 20 g of copolymer are obtained.

EXAMPLE 2

500 cm$^3$ of methanol in which 0.5 mmoles of Cu(ac)$_2$, 0.5 mmoles of 1,3-bis(diphenylphosphine)propane, 1.33 mmoles of B(C6F5)$_3$ and 40 mmoles of quinone have been previously dissolved, are charged into a 1 liter autoclave previously fluxed with nitrogen. A 1/1 molar mixture of ethylene/CO is then added until a pressure of $56 \times 10^5$ Pa is reached.

After 5 hours of reaction at 80° C., the autoclave is cooled to room temperature and the residual pressure is discharged. The copolymer is filtered, washed with methanol and dried at a temperature of about 60° C. and with a vacuum of $10^2$ Pa. 24 g of copolymer are obtained.

EXAMPLE 3

An ethylene/carbon monoxide copolymer was prepared as follows.

The catalyst was prepared by absorption, on 10 g of alternating ethylene/CO copolymer, of a catalytic solution containing: 20 cm$^3$ of methanol, 0.5 mmoles of copper(II) acetate, 0.5 mmoles of 1,3-bis(diphenylphosphine)propane, 1.5 mmoles of B(C6F5)$_3$, and 40 mmoles of quinone.

The catalyst thus prepared is charged into an 0.5 liter autoclave, stirred and maintained under a nitrogen atmosphere.

A mixture of ethylene/CO (1:1 moles) was then added until a pressure of $56 \times 10^5$ Pa was reached.

After 5 hours of reaction at 80° C., the autoclave is cooled to room temperature and the residual pressure is discharged.

The copolymer obtained is filtered, washed with methanol and dried at a temperature of about 60° C. and with a vacuum of $10^2$ Pa.

20 g of total copolymer are obtained equal to 10 g of polymer produced.

EXAMPLE 4

An ethylene/carbon monoxide copolymer was prepared as described in example 3, but with the difference that the catalytic solution contains 1.5 mmoles of borotrifluoroetherate instead of B(C6F5)$_3$.

20 g of total copolymer equal to 10 g of copolymer produced were obtained.

We claim:

1. A process, comprising copolymerizing ethylene and/or other olefinic monomers, alone or mixed with two or more monomers, with carbon monoxide to produce alternating olefin/carbon monoxide copolymers, wherein said copolymerizing is conducted in the presence of a catalytic system consisting of:

a) a Cu, Ag or Au salt, b) a bidentate chelating base containing two phosphorous or nitrogen atoms, c) a Lewis acid, and d) optionally an oxidizing agent.

2. The process of claim 1, wherein said olefinic monomers are α-olefins.

3. The process of claim 2, wherein said α-olefins are selected from the group consisting of ethylene, propylene, 1-butene, 1-pentene, cyclopentene, styrene and mixtures thereof.

4. The process of claim 1, wherein said copolymerizing is carried out in a closed reactor in a solvent at a temperature of 50°–120° C., a pressure of $40 \times 10^5$ to $100 \times 10^5$ Pa and for a polymerization time of 3–9 hours.

5. The process of claim 1, wherein said copolymerizing is conducted in the presence of a solvent and wherein the quantity of said catalyst is $10^{-2}$ to $10^{-5}$ grams-atom of Cu, Ag or Au per liter of solvent.

6. The process of claim 1, wherein said salt contains an anion selected from the group consisting of acetate, trifluoromethanesulphonate, trifluoroacetate, toxilate, sulphate, chloride, hexafluorophosphate and diethylcarbamate.

7. The process of claim 1, wherein said bidentate chelating base has the formula

$R_1R_2\text{-}M\text{-}R\text{-}M\text{-}R_3R_4$ wherein:

M is a phosphorous or nitrogen atom;

R is a polymethylene radical containing 2–4 carbon atoms, a cycloalkylidene radical containing 2–10 carbon atoms or a phenylene radical;

$R_1$, $R_2$, $R_3$, and $R_4$, which may be the same or different, are an alkyl radical containing 1–6 carbon atoms, a cycloalkyl radical containing 3–6 carbon atoms or an aromatic radical containing 6–12 carbon atoms.

8. The process of claim 1, wherein said bidentate chelating base is selected from a group consisting of 1,3-bis(diphenylphosphine)propane, 1,4-bis(dicyclohexylphosphine)butane, and 1,2-bis(diphenylphosphine)cyclohexane.

9. The process of claim 1, wherein said bidentate chelating base is 2,2'-bipyridyl.

10. The process of claim 1, wherein said bidentate chelating base is 4,4'-dimethyl-2,2'-bipyridyl.

11. The process of claim 1, wherein said Lewis acid has the formula $AX_n$, wherein n=3 or 5, or addition products thereof with bases, wherein A is B, Al, Ga, In, As, P or Sb; and X is a halogen, an aliphatic radical, an aromatic monovalent radical or a substituted aromatic monovalent radical.

12. The process of claim 1, wherein said Lewis acid is selected from the group consisting of boron trifluoride, boron trifluoride etherate, antimonium pentafluoride, arsenic pentafluoride, gallium trifluoride, aluminum trichloride, boron trichloride, boron tribromide, aluminum tribromide, tris-(pentafluorophenyl)-boron, triphenyl boron, $NaBF_4$, $NH_4PF_6$, $NaB(C_6H_5)_4$ and $NH_3R^+B(C_6H_5)_3CH_3^-$, wherein R is H, alkyl, or cycloalkyl.

13. The process of claim 12, wherein said Lewis acid is selected from a group consisting of boron trifluoride, aluminum trifluoride, and tris-(pentafluorophenyl)-boron.

14. The process of claim 1, wherein said oxidizing agent is a 1,4-quinone compound, a nitroaromatic compound, or $NOBF_4$.

15. The process of claim 1, wherein said oxidizing agent is 1,4-benzoquinone or 1,4-naphthoquinone.

16. The process of claim 1, wherein said oxidizing agent is a nitroaromatic compound.

17. The process of claim 16, wherein said nitroaromatic compound is nitrobenzene.

18. The process of claim 1, wherein component a) is a Cu salt.

19. The process of claim 1, wherein component a) is a Ag salt.

20. The process of claim 1, wherein component a) is a Au salt.

* * * * *